United States Patent
McKenna et al.

(10) Patent No.: US 6,441,214 B1
(45) Date of Patent: Aug. 27, 2002

(54) DERIVATIVES AND ANALOGS

(75) Inventors: Charles E. McKenna, Pacific Palisades; Zeng-Min Li, Alhambra; Xue-Wei Liu, Los Angeles, all of CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/352,237

(22) Filed: Jul. 13, 1999

Related U.S. Application Data
(60) Provisional application No. 60/092,650, filed on Jul. 13, 1998.

(51) Int. Cl.[7] ................................................. C07F 9/08
(52) U.S. Cl. ......................................... 558/181; 562/24
(58) Field of Search ................................. 558/179, 181; 562/8, 9, 24

(56) References Cited

U.S. PATENT DOCUMENTS

| | | | |
|---|---|---|---|
| 3,033,891 A | * | 5/1962 | Grisley et al. |
| 3,943,201 A | | 3/1976 | McIntosh |
| 4,033,749 A | * | 7/1977 | McIntosh |
| T986,003 I4 | | 9/1979 | Barrier |
| 5,072,032 A | | 12/1991 | McKenna |
| 5,183,812 A | | 2/1993 | McKenna |
| 5,869,469 A | | 2/1999 | Szarek et al. ............... 514/120 |

OTHER PUBLICATIONS

CA:97:118697 Abs of FR1479455, May 1967.*
CA:126:11358 abs of WO9639148, Dec. 1996.*
CA:124:56067 abs of Tetrahedron Lett by Salomon 36(37) pp 6759–60, 1995.*
CA:123:9544 abs of Zh Obsch Khim by Kovalenko et al 64(10) pp 1634–8, 1994.*
CA:117:69919 abs of J Org Chem by Bulpin et al 57(16) pp 4507–12, 1992.*
CA:92:175780 abs of Defensive publication US986003 H by Barrier, Sep. 1997.*
CA:72:5004 abs of Tr. Khim–Met Inst Akad Nauk Kaz SSR by Radenkova et al 5 pp 47–9, 1969.*
CA:74:112211 abs of DE 2040367, Feb. 1971.*
CA:130:154373 abs of Polym Degrad Stab by Alberti et al 62(3) pp 559–567, 1998.*
J. Levillain, et al., J. Am. Chem. Soc. 115, 8444–8446, (1993).
Grisley, D. W. Jr., J. Org. Chem. 26, 2544–2546, (1961).
Ryu, et al., J. Med. Chem. 25, 1322–1329 (1982).
Fuji, M., et al., J. Org. Chem., 62, 6804 (1997).
Irwin B. Douglass and Glenn H. Warner, J.Am.Chem.Soc., 78:6070 (1956).
Dieter Martin and Wolfgang Mocke, Chemishe Berichte, 98 (7), 2059 (1965).
Petrov, K. A., Maklyaev, F. L. and Korshunov, M. A. J. Gen. Chem. USSR (Eng. Transl.) 29, 304–308 (1959).
Kovalenko, L. V., et al., Russian J. General Chemistry 64, Part 1, 1456–1459, (1994).
Database CAPLUS on STN International (SM), Chemical Abstracts Service, (Columbus, Ohio), Accession No. 1995:400772; Kovalenko, L.V. et al. 'Synthesis of dialkoxy-phosphorylthioformic acid amides'. Zh, Obshch, Khim. 1994, vol. 64, No. 10, pp. 1639–1641, abstract.
Database, CAPLUS on STN International (SM), Chemical Abstracts Service, (Columbus, Ohio), Accession No. 1995: 400771; Kovalenko, L.V. et al. 'Synthesis of phosphono-thioformate esters'. Zh, Obshch. Khim. 1994, vol. 64, No. 10, pp. 1634–1638, abstract.
P. Wutzler, Therapeutic effect of pyrophosphate analogues on cutaneous herpes simplex virus type 1 infection in guinea pigs. Antiviral Research, 1988, vol. 10, pp. 99–106, expecially p. 101, Figure 1.
Database CAPLUS on STN International (SM), Chemical Abstracts Service, (Columbus, Ohio), Accession No. 1993:168; Straw, J.A. et al. 'Pharmacokinetics of potential anti–AIDS agents thiofoscarnet and foscarnet in the cat'. J. Acquired Immune Defic. Syndr. 1992, vol. 5, No. 9, pp. 936–942, abstract.
Zao–Yuan Peng, Joan M. Mansour, Fausto Araujo, Jing–Yue Ju, Charles E. McKenna and Tag E. Mansour—Some Phosphonic Acid Analogs as Inhibitors of Pyrophosphate–Dependent Phoshofructokinase, *A Novel Target in Toxoplasma Gondii*, Biochemical Pharmacology, vol. 49, No. 1, pp. 105–113, 1995.
Kabachnik, M.I. et al. Reactions of chloroacetyl chloride, tricholoroacetyl chloride, and phosgene with trialkyl phosphites. Izvest. Akad Nauk S.S.S.R., Otdel. Khim. Nauk. 1957, pp. 48–53, abstract. Chemical Abstracts, vol. 51, 1957, 10366.
Ismailov, V.M. et al. Database CAPLUS on STN International Sm. Chemical Abstracts Service, (Columbus, Ohio) Accession No. 1981:97911; *Some Transformations of Substituted Vinyl Phosphonates*, Azerb, Khim. Zh. 1980, No. 3, pp. 58–63, abstract.

* cited by examiner

*Primary Examiner*—Jean F. Vollano
(74) *Attorney, Agent, or Firm*—Fulbright & Jaworski LLP

(57) ABSTRACT

Preparation of phosphonoformic acid analogues containing one, two, three, or more sulfur atoms are described, with specific examples. Such compounds, not excluding cognates, derivatives, and homologues thereof, are proposed to be used directly, or as prodrugs, in treating viral infections, including but not limited to HIV, herpesviruses including HSV, EBV, VZV, CMV, HSV-6 and HSV-8 (Kaposi's sarcoma); HPV; rhinoviruses; and hepatitis-linked viruses. They are also proposed to be used in treating neoplasms, and for diagnosis and therapy of diseases of bone metabolism. The compounds of the present invention are also designed as to create novel biologically active compounds or prodrugs.

5 Claims, No Drawings

DERIVATIVES AND ANALOGS

CROSS-REFERENCE WITH RELATED APPLICATIONS

This application claims the benefit of U.S. Provisional Application No. 60/092,650, filed Jul. 13, 1998.

BACKGROUND OF THE INVENTION

1. Field of the Invention

The invention relates generally to the field of phosphorus chemistry, and is particularly concerned with a novel method for the production of sulfur-containing phosphonoformates and their derivatives. An additional aspect of the present invention relates to the use of these compounds as antiviral agents, including: Human Immunodeficiency Virus (HIV); herpes viruses including, Herpes Simplex Virus (HSV), Ebstein-Barr Virus (EBV), Varicella Zoster Virus (VZV), Cytomegalovirus (CMV), HSV-6, and HSV-8 (Kaposi's sarcoma); Human Papilloma Virus (HPV); rhinoviruses; and hepatitis-linked viruses.

2. Description of Related Art

A retrovirus designated HIV is believed to be the causative agent of the complex disease termed Acquired Immune Deficiency Syndrome (AIDS). The complex disease AIDS includes progressive destruction of the immune system and degeneration of the central and peripheral nervous system. The HIV virus appears to preferentially attack helper T-cells (T-lymphocytes or OKT4-bearing T-cells) and also other human cells, e.g., certain cells within the brain. The helper T-cells are invaded by the virus and the T-cells become an HIV virus producer. The helper T-cells are quickly destroyed and their number in the human being is depleted to such an extent that the body's B-cells as well as other T-cells normally stimulated by the helper T-cells no longer function normally or produce sufficient lymphokines and antibodies to destroy the invading virus or other invading microbes.

While the HIV virus does not necessarily cause death per se, it does cause severe damage to the human immune system resulting in the onset of various other opportunistic diseases such as, herpes, toxoplasmosis, cytomegalovirus (CMV), Kaposi's sarcoma, and EBV related lymphomas, among others, (AIDS). HIV virus infected individuals, at first, experience few or no symptoms. Later in the disease, the onset of immune system dysfunction occurs, leading to various symptoms such as weight loss, malaise, fever, and swollen lymph nodes (AIDS related complex). The disease further progresses to full blown AIDS, leading usually to death. Those infected with the HIV virus are persistently infective to others.

Unfortunately, the present state of the art is such that antiviral drugs are only capable of attacking such viruses when they are replicating. Attacking a latent virus such as HIV, which does not reproduce itself following infection until reactivated by presently unknown factors would require distinguishing the viral genetic material from the surrounding host genetic material and selectively destroying it. Thus, the current generation of antiviral drugs is only effective against replicating viruses. Considerable efforts are being directed toward the control of HIV by means of inhibition of the reverse transcriptase of HIV and of other targets of viral functions, required for replication of the virus. Unfortunately, many of the known compounds suffer from toxicity problems, lack of bioavailability or are short-lived in vivo, viral resistance, or combinations thereof. Particularly important is combined therapy agents targeting more than one viral function. The requirement for development of new drugs able to be used in combination with other types of drugs is important in continued HIV therapy.

Several researchers have indicated that the pyrophosphonate analogues, such as phosphonoformic acid (PFA) and its analogues and derivatives possess antiviral properties in that they inhibit the replication of several viruses. (See, U.S. Pat. Nos. 5,072,032 and 5,183,812 to McKenna; D. W. Hutchinson, et al., Synthesis and Biochemical Properties of Some Pyrophosphate Analogues, *Biophosphates and Their Analogues-Synthesis, Structure, Metabolism and Activity,* K. S. Bruzik and W. J. Stec (Eds.), Elsevier Science Publishers, B. V., 1987, 441–450;. and Helgstrands, et al., *Science,* 201:819–821 (1978)). Trisodium phosphonoformate (PFA, Foscarnet), a pyrophosphate analog, has been reported to inhibit HIV reverse transcriptase (HIV, RT) with an $ID_{50}$ near 1 μm, and has also been reported to inhibit several herpes virus DNA polymerases, including the DNA polymerase of CMV. See, U.S. Pat. No. 5,072,032 to McKenna.

Previous studies reported the addition of nucleophiles to the thiocarbonyl group. (See, J. Levillain, et al., *J. Am. Chem. Soc.* 115, 8444-8446, 1993; and L. V. Kovalenko, et al., *Russian J. General Chemistry* 64, Part 1, 1456–1459, 1994). Preparations of thiocaibonyl and dithiocarboxyl derivatives have been demonstrated in the reaction of trialkyl phosphate and chlorothioformate. (See, D. W. Grisley, Jr., *J. Org. Chem.* 26, 2544–2546, 1961.) However, trimethyl phosphonoformate thio derivatives have not been previously reported, except trimethyl thiophosphonoformate, U.S. Pat. No. 5,072,032 to C. E. McKenna, et al., and trimethyl phosphonothionoformate, Kovalenko et al., supra. Corresponding monosodium salts and trisodium salts are, disclosed for the first time, except for the monosodium and trisodium salts of thiophosphonoformate which were previously disclosed McKenna, et al, supra.

BRIEF SUMMARY OF THE INVENTION

The present invention solves the above-described problems by providing methods for readily synthesizing sulfur-containing phosphonoformic acid derivatives and the use of such derivatives as chemotherapeutic agents. In one embodiment of the invention, sulfur-containing phosphonoformate derivatives are obtained formally by replacing one or more of the five oxygen atoms of the original phosphonoformate molecule by a sulfur atom. Another embodiment of the present invention is a method for synthesizing polyhydroxy derivatives of such analogs. The method uses the base compound (foscarnet), but can be extended to prepare similar derivatives based on the thio analogues of foscarnet. An additional aspect of the present invention relates to the use of these compounds as antiviral agents, including: HIV and herpes viruses.

These and other features, aspects, and advantages of the present invention will become better understood with regard to the following detailed description and appended claims.

DETAILED DESCRIPTION OF THE INVENTION

The present invention teaches the synthesis of sulfur-containing phosphonoformic acid derivatives, which are obtained by replacing one or more of the five oxygen atoms of the original phosphonoformate molecule by a sulfur atom, see TABLE I. CAS is the Chemical Abstract Service.

TABLE I

Selected Phosphonoformate Thio-Analogues

| Name | Structure |
|---|---|
| Na₃TPFA, 1 | (NaS)(NaO)P(=O)–C(=O)–ONa |
| NaTPFA, 6 | (NaO)(CH₃S)P(=O)–C(=O)–OCH₃ |
| NaPTNFA, 7 | (NaO)(CH₃O)P(=O)–C(=S)–OCH₃ |
| NaPTLFA, 8 | (NaO)(CH₃O)P(=O)–C(=O)–SCH₃ |
| NaPDTFA, 9 | (NaO)(CH₃O)P(=O)–C(=S)–SCH₃ |
| NaTPTNFA, 10 | (NaO)(CH₃S)P(=O)–C(=S)–OCH₃ |
| NaTPTLFA, 11 | (NaO)(CH₃S)P(=O)–C(=O)–SCH₃ |
| NaTPDTFA, 12 | (NaO)(CH₃S)P(=O)–C(=S)–SCH₃ |

TABLE I-continued

Selected Phosphonoformate Thio-Analogues

| Name | Structure |
|---|---|
| Me₃TPFA, 13 | (CH₃O)₂P(=S)–C(=O)–OCH₃ |
| Me₃PTNFA, 14 | (CH₃O)₂P(=O)–C(=S)–OCH₃ |
| Me₃PTLFA, 15 | (CH₃O)₂P(=O)–C(=O)–SCH₃ |
| Me₃PDTFA, 16 | (CH₃O)₂P(=O)–C(=S)–SCH₃ |
| Me₃TPTLFA, 17 | (CH₃O)₂P(=S)–C(=O)–SCH₃ |
| Me₃TPTNFA, 18 | (CH₃O)₂P(=S)–C(=S)–OCH₃ |
| Me₃TPDTFA, 19 | (CH₃O)₂P(=S)–C(=S)–SCH₃ |

General synthetic pathways as applied to examples of various thio-analogs of PFA are outlined in the following conceptual schemes:

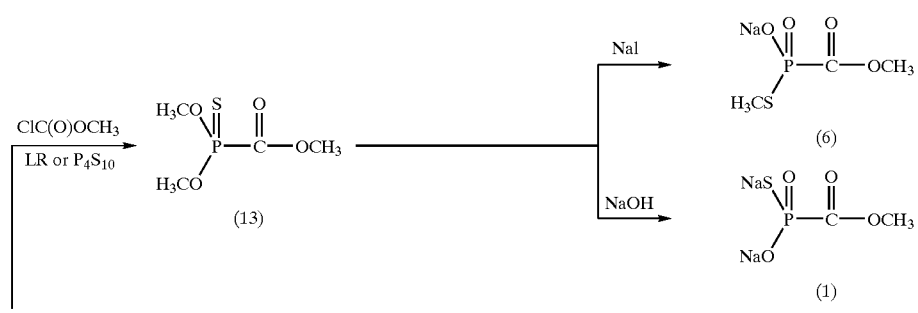

-continued

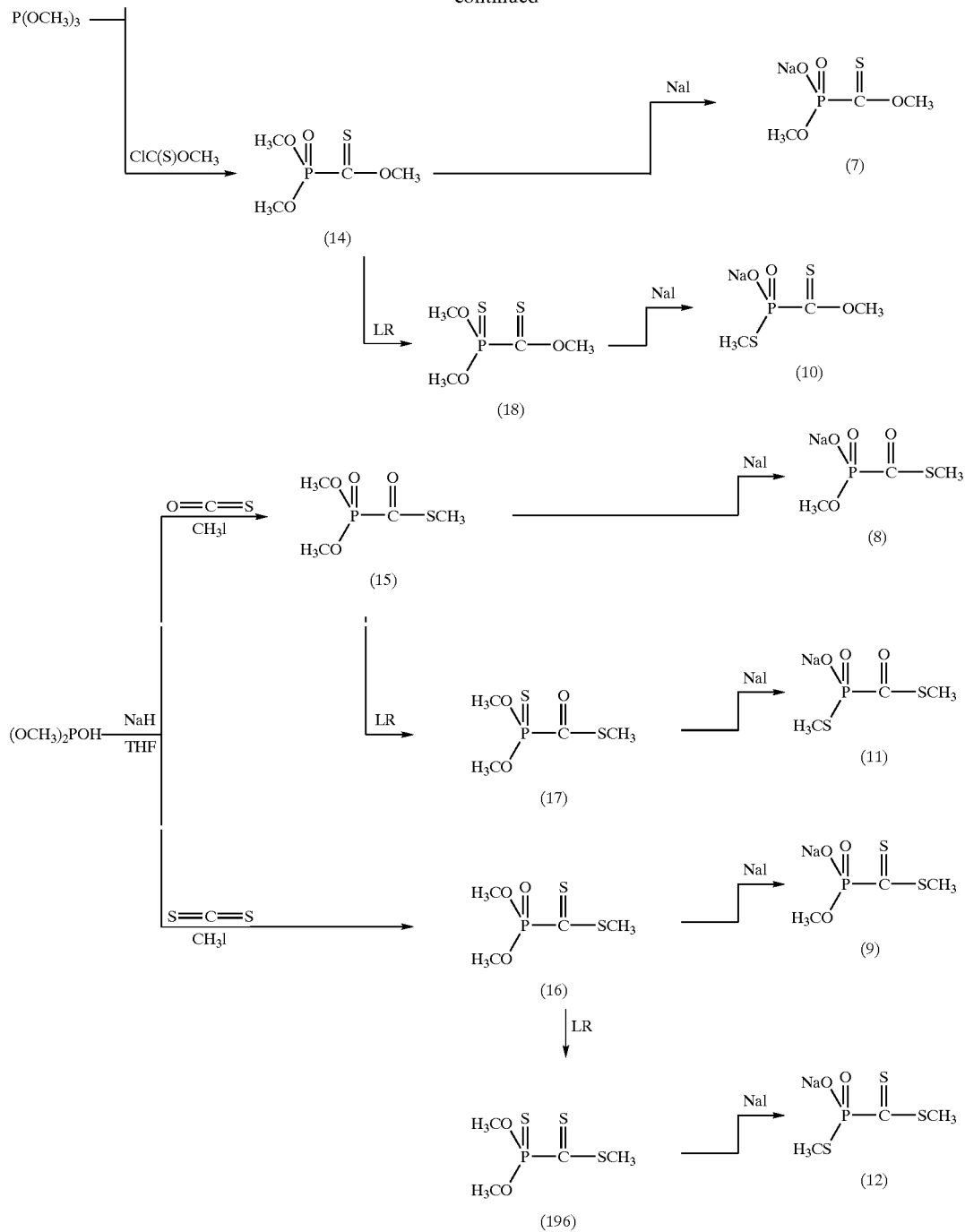

The unique biological activities of the compounds disclosed herein, and their corresponding classes, derive chiefly from two factors: 1) modification of their reactivity, cell transport, cell permeation, metabolism, and enzyme or membrane receptor site binding properties due to the different chemical and physical properties of sulfur relative to oxygen; and 2) potential in situ physiological conversion of S to O, creating the possibility of prodrugs for which the actual drug has one or more S converted to O after administration. Another factor is the modified properties of prodrugs or other analogues in which the sulfur-containing function is derivatized, e.g. as an ester, ether, etc., relative to metabolic activation in vivo.

Thio-Analogues of PFA

The analogues have the general structure:

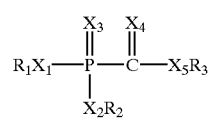

$R_1$ and $R_2$ are each independently selected from alkyl, aryl, H, or cation, $R_3$ is independently selected from alkyl, aryl, H, or cation:

$X_1$, $X_2$, $X_3$, $X_4$, and $X_5$ are O or S, provided that:
(a) at least one of $X_1$–$X_5$ is S;
(b) when $X_1$ is S, then either (i) $R_1$ or $R_2$ is alkyl, aryl, or H, or (ii) at least one of $X_2$, $X_3$, $X_4$, and $X_5$ is also S.

The parent structures may form part of a derived entity wherein $R_1$, $R_2$ and/or $R_3$ are more complex molecules than simple alkyl or aryl compounds (or portions of the same molecule), with the parent incorporated via one or more esteratic or ether bonds as indicated above. The cation can be a pharmaceutically acceptable alkali metal (e.g., Li, Na, or K), ammonium cation; alkaline earth cation (e.g., $Ca^{2+}$, $Ba^{2+}$, $Mg^{2+}$), higher valency cation, or polycationic counter ion (e.g., a polyamonium cation). See, Berge, et al., "Pharmaceutical Salts", *J. Pharm. Sci.* (1977) 66:1–19. It will be appreciated that the stoichiometry of an anionic compound to a salt-forming counterion (if any) will vary depending on the charge of the anionic portion of the compound (if any) will vary depending on the charge of the anionic portion of the compound (if any) and the charge of the counterion. Preferred pharmaceutically acceptable salts include a sodium, potassium or calcium salt, but other salts are also contemplated within their pharmaceutically acceptable range. Furthermore $R_1$, $R_2$, and $R_3$ may be so designed as to create novel biologically active compounds or prodrugs, wherein one conjugating moiety may be for example a nucleoside or nucleotide with independent activity, and another moiety may be for example a diol, triol or higher polyhydroxy group conferring enhanced cell transport or other desirable properties.

Classes of Parent Structures ($X_1$–$X_5$=O Except as Noted)

The following compilation sets forth permutations for illustrative purposes. It will be appreciated that simple experiments by those skilled in the art will readily eliminate those compounds that are not stable or are synthetically unattainable.

A. Triesters: $R_1$, $R_2$, $R_3$ = alkyl, aryl or complex

A.1: Monothio Analogues

| | |
|---|---|
| $X_1$ = S | (A.1.a) |
| $X_3$ = S | (A.1.b) |
| $X_4$ = S | (A.1.c) |
| $X_5$ = S | (A.1.d) |

A.2: Dithio Analogues

| | |
|---|---|
| $X_1$, $X_2$ = S | (A.2.a) |
| $X_1$, $X_3$ = S | (A.2.b) |
| $X_1$, $X_4$ = S | (A.2.c) |
| $X_1$, $X_5$ = S | (A.2.d) |
| $X_3$, $X_4$ = S | (A.2.e) |
| $X_3$, $X_5$ = S | (A.2.f) |
| $X_4$, $X_5$ = S | (A.2.g) |

A.3: Trithio Analogues

| | |
|---|---|
| $X_1$, $X_2$, $X_3$ = S | (A.3.a) |
| $X_1$, $X_2$, $X_4$ = S | (A.3.b) |
| $X_1$, $X_2$, $X_5$ = S | (A.3.c) |
| $X_1$, $X_3$, $X_4$ = S | (A.3.d) |
| $X_1$, $X_3$, $X_5$ = S | (A.3.e) |
| $X_1$, $X_4$, $X_5$ = S | (A.3.f) |
| $X_3$, $X_4$, $X_5$ = S | (A.3.g) |

A.4: Tetrathio Analogues

| | |
|---|---|
| $X_1$, $X_2$, $X_3$, $X_4$ = S | (A.4.a) |
| $X_1$, $X_2$, $X_3$, $X_5$ = S | (A.4.b) |
| $X_1$, $X_2$, $X_4$, $X_5$ = S | (A.4.c) |
| $X_1$, $X_3$, $X_4$, $X_5$ = S | (A.4.d) |

A.5: Pentathio Analogues

| | |
|---|---|
| $X_1$, $X_2$, $X_3$, $X_4$, $X_5$ = S | (A.5.a) |

Note: where $R_1$ = $R_2$, $X_1$ and $X_2$ are equivalent substitutions. However, compounds wherein $R_1$ = $R_2$, such that $X_1$ and $X_2$ substitutions result in distinct isomers, are also within the scope of the invention. Furthermore, steroisomers, including stereoisomers created by the possibility of chirality at the phosphorus atom e.g. in a structural fragment like $M^+[R_1O(S)P(O)R_3]^-$ where $M^+$ is a cation are also within the scope of the invention.

B. Diesters

B.1: Monothio Analogues $R_1$, $R_3$ = alkyl/aryl/complex:

| | |
|---|---|
| $X_1$ = S | (B.1.a) |
| $X_2$ = S | (B.1.b) |
| $X_4$ = S | (B.1.c) |
| $X_5$ = S | (B.1.d) |

$R_1$, $R_2$ = alky/aryl/complex:

| | |
|---|---|
| $X_1$ = S | (B.1.e) |
| $X_3$ = S | (B.1.f) |
| $X_4$ = S | (B.1.g) |

Note: where unspecified, $R_1$, $R_2$, and $R_3$ are $H^+$ or other cations.

B.2: Dithio Analogues $R_1$, $R_3$ = alkyl/aryl/complex:

| | |
|---|---|
| $X_1$, $X_2$ = S | (B.2.a) |
| $X_1$, $X_4$ = S | (B.2.b) |
| $X_1$, $X_5$ = S | (B.2.c) |
| $X_2$, $X_3$ = S | (B.2.d) |
| $X_2$, $X_4$ = S | (B.2.e) |
| $X_2$, $X_5$ = S | (B.2.f) |
| $X_4$, $X_5$ = S | (B.2.g) |

$R_1$, $R_2$ = alkyl/aryl/complex:

| | |
|---|---|
| $X_1$, $X_2$ = S | (B.2.h) |
| $X_1$, $X_3$ = S | (B.2.i) |
| $X_1$, $X_4$ = S | (B.2.j) |
| $X_3$, $X_4$ = S | (B.2.k) |

B.3: Trithio Analogues $R_1$, $R_3$ = alkyl/aryl/complex:

| | |
|---|---|
| $X_1$, $X_2$, $X_4$ = S | (B.3.a) |
| $X_1$, $X_2$, $X_5$ = S | (B.3.b) |
| $X_2$, $X_3$, $X_4$ = S | (B.3.c) |
| $X_2$, $X_3$, $X_5$ = S | (B.3.d) |

$R_1$, $R_2$ = alkyl/aryl/complex:

| | |
|---|---|
| $X_1$, $X_2$, $X_3$ = S | (B.3.e) |
| $X_1$, $X_2$, $X_4$ = S | (B.3.f) |
| $X_1$, $X_3$, $X_4$ = S | (B.3.g) |
| $X_3$, $X_4$, $X_5$ = S | (B.3.h) |

B.4: Tetrathio Analogues $R_1$, $R_3$ = alkyl/aryl/complex:

| | |
|---|---|
| $X_1$–$X_4$ = S | (B.4.a) |
| $X_1$–$X_3$, $X_5$ = S | (B.4.b) |
| $X_2$–$X_5$ = S | (B.4.c) |
| $X_1$, $X_3$–$X_5$ = S | (B.4.d) |

$R_1$, $R_2$ = alkyl/aryl/complex:

| | |
|---|---|
| $X_1$–$X_4$ = S | (B.4.e) |
| $X_2$–$X_5$ = S | (B.4.f) |
| $X_1$, $X_2$, $X_4$, $X_5$ = S | (B.4.g) |

-continued

B.5: Pentathio Analogues $R_1, R_3$ = alkyl/aryl/complex:

$X_1–X_5 = S$          (B.5.a)

$R_1, R_2$ = alkyl/aryl/complex:

$X_1–X_5 = S$          (B.5.b)

C. Monoesters:

C.1: Monothio Analogues $R_1$ = alkyl/aryl/complex:

$X_1 = S$          (C.1.a)
$X_2 = S$          (C.1.b)
$X_4 = S$          (C.1.c)

$R_3$ = alkyl/aryl/complex:

$X_1 = S$          (C.1.d)
$X_4 = S$          (C.1.e)
$X_5 = S$          (C.1.f)

C.2: Dithio Analogues $R_1$ = alkyl/aryl/complex:

$X_1, X_2 = S$          (C.2.a)
$X_1, X_4 = S$          (C.2.b)
$X_1, X_5 = S$          (C.2.c)
$X_2, X_4 = S$          (C.2.d)
$X_4, X_5 = S$          (C.2.e)

$R_3$ = alkyl/aryl/complex:

$X_1, X_2 = S$          (C.2.f)
$X_1, X_4 = S$          (C.2.g)
$X_1, X_5 = S$          (C.2.h)
$X_4, X_5 = S$          (C.2.i)

C.3: Tetrathio Analogues $R_1$ = alkyl/aryl/complex:

$X_1–X_4 = S$          (C.3.a)
$X_2–X_5 = S$          (C.3.b)
$X_1, X_3–X_5 = S$          (C.3.c)

$R_3$ = alkyl/aryl/complex:

$X_1–X_4 = S$          (C.3.d)
$X_1–X_3, X_5 = S$          (C.3.e)
$X_1, X_3–X_5 = S$          (C.3.f)

C.4: Pentathio Analogues $R_1$ = alkyl/aryl/complex:

$X_1–X_5 = S$          (C.4.a)

$R_3$ = alkyl/aryl/complex:

$X_1–X_5 = S$          (C.4.b)

D: Triacids and Salts:

D.1: Monothio Analogues $X_1 = S$          (D.1.a)
$X_4 = S$          (D.1.b)

D.2: Dithio Analogues $X_1, X_2 = S$          (D.2.a)
$X_1, X_4 = S; X_4, X_5 = S$          (D.2.b)

D.3: Trithio Analogues $X_1–X_3 = S$          (D.3.a)
$X_1, X_3, X_4 = S$          (D.3.b)
$X_1, X_4, X_5 = S$          (D.3.c)

D.4: Tetrathio Analogues $X_1–X_4 = S$          (D.4.a)
$X_1, X_3–X_5 = S$          (D.4.b)

D.5: Pentathio Analogues $X_1–X_5 = S$          (C.5.h)

In accordance with this invention, TPFA is conjugated with polyalcohols. We postulate that such compounds can have enhanced membrane transport properties, and thus higher activity than the parent in vivo. Some 15 years ago, oral delivery of different classes of drugs was shown to be facilitated by incorporation of 1-O-alkyl, 1-O-acyl-sn-glycerol-phosphate moieties. See, Ryu, et al., *J. Med. Chem.* 25, 1322–1329 (1982). More recent examples of this approach have been given by M. Fuji,.et al., *J. Org. Chem.*, 62, 6804 (1997) and by K. Hostetler, et al., *Antiviral Research*, 31, 59–67 (1996).

Our proposed synthetic routes are illustrated in the examples below.

Scheme II

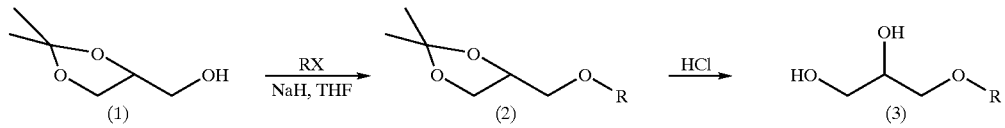

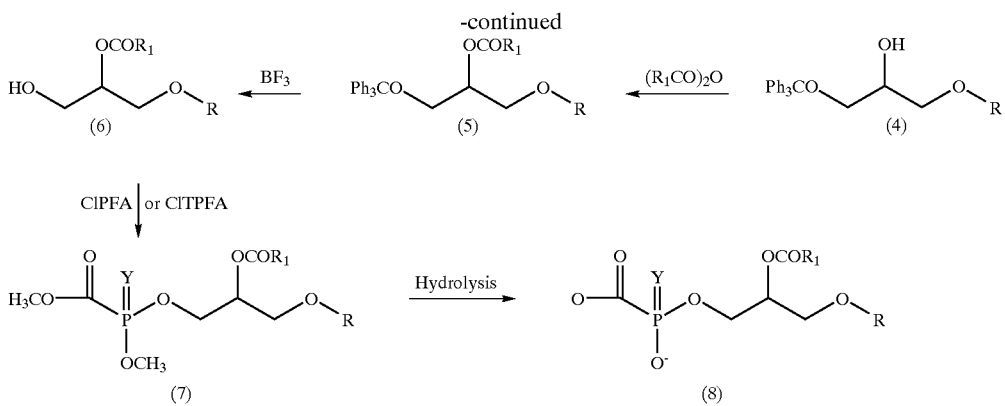

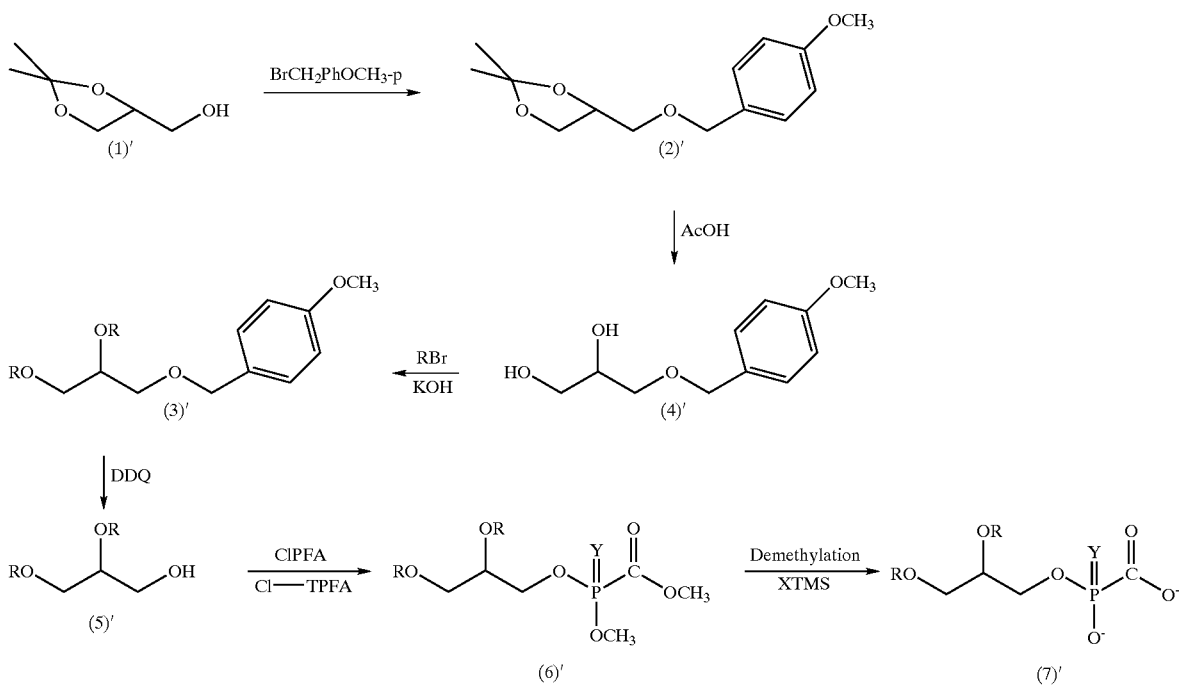

R = alkyl, aryl, e.g., C₃H₇, C₁₆H₃₃
R = alkyl, e.g., CH3
Y = O or S

Wherein $R_1$ is alkyl, such as $C_3H_7$ or $C_{16}H_{33}$; $R_2$ is alkyl, such as $CH_3$; and Y is O or S.

General Experimental Protocol

Solvents for reactions were purified as follows: THF was distilled from sodium and benzophenone ketyl, toluene was distilled from $CaH_2$, and acetone was dried with molecular sieve. Solvents for column chromatography or Thin Layer Chromatography (TLC) were not pretreated. The end points of all reactions were checked using TLC or NMR except noted. Monosodium salts and trisodium salts were dried in a vacuum, and all the products were stored at 4° C. $R_1$ is an alkyl group having 1 to 22 carbon atoms. $R_2$ is an alkyl group having 1 to 6 carbon atoms. X is a halogen, such as chlorine, bromine, and iodine.

All solvents and reagents were of Analytical Reagent (AR) grade quality, purchased from. Sigma-Aldrich,. Inc., without further purification except where noted. Nuclear Magnetic Resonance (NMR) spectra were recorded on $CDCl_3$ solutions for triesters and on $D_2O$ for monosodium salts and trisodium salts. $^1H$ and $^{13}C$ spectra were recorded on Bruker AC250 MHz or AM360 MHz spectrometers, in $CDCl_3$. $^1H$ chemical shifts are referenced to $CHCl_3$ ($\delta 7.24$). $^{13}C$ chemical shifts were referenced to: $CDCl_3$ ($\delta 77.0$); $D_2O$ HDO ($\delta 4.63$); and $C_6D_6$ ($\delta 128$). $^{31}P$ spectra were recorded on the 360 MHz instrument. $^{31}P$ NMR chemical shifts are referenced to external 85% $H_3PO_4$. Chemical shifts are reported in ppm (s=singlet, d=doublet, t-triplet, q=quartet, m=multiplet). High Resolution Mass Spectra (HRMS) determinations were performed at UC Riverside.

A. Synthetic Procedures for Trimethyl Esters

EXAMPLE 1

S-Methyl (Dimethylphosphinyl)thioformate

S-Methyl (Dimethylphosphinyl)thioformate, Table I Compound (15), was prepared by a previously published method (Kovalenko, et al., *Russian Journal of General Chemistry*, 64 (10) Part 1, 1456, (1994)). A solution of 1.00 g (9 mmol) of S-methyl chlorothioformate in 5 mL of dry toluene was added over 10 min to a solution of 1.12 g (9 mmol) of trimethyl phosphite in 10 mL of dry toluene. The mixture was stirred and maintained below 30° C. for 2 h. Toluene was removed by rotary evaporation under reduced pressure, and the resulting residue was distilled in vacuo, giving 0.72 g of a colorless oil, b.p.: 78–80° C./20μ. The yield of product was about 55.6%.

EXAMPLE 2

S-Methyl (Dimethylphosphinyl)thioformate, Table I Compound (15), was prepared by a previously published method (Grisley, D. W., Jr., *J. Org. Chem.* 26:2544, (1961)). 11.0 g (0.1 mole) of dimethyl phosphite was added dropwise to a stirred solution of 2.4 g (0.1 mole) of sodium hydride in 50 mL of dry THF at 25–30° C. under $N_2$. The mixture was stirred and refluxed until $H_2$ evolution ceased. The mixture was then cooled to 6° C. and carbonyl sulfide gas was passed into the mixture until 6.7 g (0.11 mole) was absorbed. Methyl iodide (14.2 g, 0.1 mole) was then added at 5° C. over 15 min. The mixture was poured into 350 ml of ice-water and extracted with ether (3×100 mL). The ether layers were combined, dried with anhydrous magnesium sulfate, filtered, evaporated to remove ether and distilled in vacuo. The fraction boiling between 87–89° C./100μ was collected, 5.9 g, Y=32.1%. $_1$H NMR: δ (ppm) 3.87 (d, 6H, $^3J_{HP}$=11 Hz, POCH$_3$), 2.40 (d, 3H, $^4J_{HP}$=1 Hz, CSCH$_3$); $^{13}$C NMR: δ (ppm 197.7 (d, $^1J_{CP}$=208 Hz, CO), 54.6 (d, $^2J_{CP}$=7 Hz, POCH$_3$), 11.0 (d, $^3J_{CP}$=4 Hz, CSCH$_3$); $^{31}$P NMR: δ (ppm) –1.44 (m, $^3J_{PH}$=11 Hz); $^{31}$P NMR {H}: δ (ppm) –1.44 (s); HRMS: 185.0041 (MH$^+$, Found), 185.0037 (MH$^+$, Calcd).

EXAMPLE 3

Methyl (Dimethoxyphosphinyl)thioformate, Table I Compound (14)

O-methyl chlorothioformate was prepared as follows: To a stirred solution of 40 g sodium hydroxide, 150 mL of water and 200 mL of methanol, cooled by means of an ice-bath, carbon disulfide (24 mL) was added dropwise over a 1 hour period. The mixture was treated with 0.1 g of KI and chlorine gas passed in until the purple color of free iodine was observed (end-point). The iodine color was discharged with 10% NaHCO$_3$. The mixture was washed with water (3×50 mL) and dried with CaCl$_2$. After filtration, a yellowish-green crude oil was obtained. $^1$H NMR: δ (ppm) 4.22. [See, Irwin B. Douglass and Glenn H. Warner, *J.Am.Chem.Soc.*, 78:6070 (1956)].

While cooled externally with cold water, 34 g of the crude oil described above was treated with 9 g of chlorine. The temperature should not exceed 30° C. to avoid over-chlorination. The mixture was heated slowly, then fractionated. The fraction boiling at 84–86° C./760 mm was collected, giving 12.7 g of O-methyl chlorothioformate, Y=72%. $_1$H NMR: δ (ppm) 4.16. [See, Dieter Martin and Wolfgang Mocke, *Chemishe Berichte*, 98 (7), 2059 (1965).[4]]

A solution of 0.55 g (5 mmol) of O-methyl chlorothioformate in 8 mL of dry toluene was added over 10 min to a solution of 0.62 g (5 mmol) trimethyl phosphite in 15 mL of dry toluene under $N_2$. The mixture was stirred and left for 2 hr at room temperature. The solvent was rotary-evaporated, and the residue distilled in vacuo, giving 0.52 g of a yellow oil, 80–81° C./100μ, Y=56.5%. $^1$H NMR: δ (ppm) 4.18 (d, 3H, $^4J_{HP}$=2 Hz, COCH$_3$), 3.87 (d, 6H, $^3J_{HP}$=11 Hz POCH$_3$); $^{13}$C NMR: δ (ppm) 212.5 (d, $_1J_{CP}$=223 Hz, PC), 59.1 (d, $^2J_{CP}$=8 Hz, POCH$_3$), 54.8 (d, $^3J_{CP}$=6 Hz, COCH$_3$); $^{31}$P NMR {H}: δ (ppm) –1.14 (s); $^{31}$P NMR: δ (ppm) –1.14 (m, $^3J_{PH}$=11 Hz); HRMS: 185.0031 (MH$^+$, Found); 185.0037 (MH$^+$, Calcd).

EXAMPLE 4

Methyl (Dimethoxyphosphinyl)dithioformate. Table I Compound (16)

Dimethyl phosphite (11.0 g 0.1 mol) was added dropwise to a stirred solution of 2.4 g (0.1 mole) of sodium hydride in 50 mL of dry THF at 25–30° C. under $N_2$. The mixture was stirred under reflux until $H_2$ evolution ceased. It was then cooled to 6° C. and was added with stirring to carbon disulfide (38 g, 0.5 mol) at 2–8° C. over 15 min. Methyl iodide (14.2 g 0.1 mol) was then added at 5° C. over 15 min. The mixture was quenched with 350 mL of ice-water and extracted with ether (100 mL×3). The ether layers were combined, dried with anhydrous magnesium sulfate, filtered, evaporated to remove ether and distilled in vacuo. The fraction boiling between 92–94° C./50μ was collected, 6.5 g, Y=32.5%. (Put footnote 2 here) $^1$H NMR: δ (ppm) 3.85 (d, 6H, $^3J_{HP}$=10 Hz, POCH$_3$), 2.69 (d, 3H, $J_{HP}$=1 Hz CSCH$_3$); $^{13}$C NMR: δ (ppm) 228(d, $^1J_{CP}$=175 Hz, CS), 54.5 (d, $^2J_{CP}$=6 Hz, POCH$_3$), 10.9 (s, CSCH$_3$); $^{31}$P NMR {H}: δ (ppm) 0.30 (s); $^{31}$P NMR: δ (ppm) 0.30 (m, $^3J_{PH}$=11 Hz); HRMS: 199.9732 (Found); 199.9731 (Calcd).

EXAMPLE 5

The process of Example 4 was repeated for Methyl (Dimethoxythiophosphinyl)formate, Table I Compound (13), with the following results: $^1$H NMR: δ (ppm) 3.89 (s, 3H, COCH$_3$), 3.79 (d, 6H, $^3J_{PH}$=13 Hz POCH$_3$); $^{13}$C NMR: δ (ppm) 167.5 (d, $^1J_{CP}$=227 Hz, CO), 54.5 (d, $^2J_{CP}$=6 Hz, POCH$_3$), 52.9 (s, COCH$_3$); $^{31}$P NMR {$^1$H}: δ (ppm) 64.9. This is a compound previously described in McKenna's U.S. Pat. Nos. 5,072,032 and 5,183,812.

EXAMPLE 6

The process of Example 4 was repeated for S-Methyl (Dimethoxythiophosphinyl)thioformate, Table I Compound (17), with the following results: $^1$H NMR: δ (ppm) 3.85 (d, $^3J_{HP}$=12 Hz, 6H, POCH$_3$), 2.39 (d, $^3J_{HP}$=12 Hz, 3H, CSCH$_3$); $^{13}$C NMR: δ (ppm) 198.4 (d, $^1J_{CP}$=163 Hz, CS), 54.6 (d, $^2J_{CP}$=6 Hz, POCH$_3$), 11.6 (s, CSCH$_3$); $^{31}$P NMR: δ (ppm) 68.0 ($^3J_{PH}$=12 Hz); HRMS: 200.9827 (MH+, Found); 200.9809 (MH+, Calcd).

EXAMPLE 7

The process of Example 4 was repeated for Methyl (Dimethoxythiophosphinyl)thioformate, Table I Compound (18), with the following. results: NMR: $^1$H: δ (ppm) 4.19 (s, 3H, COCH$_3$), 3.87 (d, 6H, $^3J_{PH}$=11 Hz POCH$_3$); $^{13}$C NMR: δ (ppm) 214.5 (d, $^2J_{CP}$=180 Hz, CS), 59.5 (d, $^2J_{CP}$=9 Hz, POCH$_3$), 55.0 (d, $J_{CP}$=7 Hz, COCH$_3$); $^{31}$P NMR {$^1$H}: δ (ppm) 67.2; HRMS: 200.9815 (MH+, Found); 200.9809 (MH+, Calcd).

EXAMPLE 8

The process of Example 4 was repeated for Methyl (Dimethoxythiophosphinyl)dithioformate, Table I Compound (19), with the following results: $^1$H NMR: δ (ppm) 3.89 (d, 6H, $^3J_{HP}$=13 Hz, POCH$_3$), 2.67 (d, 3H, $^4J_{HP}$=4 Hz, CSCH$_3$), $^{13}$C. NMR: δ (ppm) 231.0 (d, $^1J_{CP}$=136 Hz, CS), 55.0 (d, $^2J_{CP}$=7 Hz, POCH$_3$), 19.8 (d, $^3J_{CP}$=3 Hz, CSCH$_3$); $^{31}$P NMR {H}: δ (ppm) 70.0; $^{31}$P NMR: δ (ppm) 70.0 (m, $^3J_{PH}$=11 Hz); HRMS: 216.9581 (Found); 216.9581 (Calcd). Microanalysis: C%: 22.22 (Calcd), 22.24 (Found); H%: 4.19 (Calcd), 4.25 (Found).

EXAMPLES 9 TO 11

General Procedure (using Lawesson's Reagent, LR) LR (7.2 g, 17.8 mmol) was weighed out in a Dry Box and suspended in 100 mL of dry toluene. Trimethyl phosphonoformate, (11.4 mmol) in 10 mL of dry toluene was added. The mixture was refluxed for 6 h. The solid by-product was filtered, and toluene removed in vacuo. The residue was extracted with 40 mL of dry hexane, and the extract filtered, evaporated and distilled in vacuo to give the desired product.

EXAMPLE 9

The preceding general procedure was followed wherein the Me$_3$PTLFA was substituted for trimethyl phosphonoformate.

EXAMPLE 10

The preceding general procedure was followed wherein the Me$_3$PTNFA was substituted for trimethyl phosphonoformate.

EXAMPLE 11

The preceding general procedure was followed wherein the Me$_3$PDTFA was substituted for trimethyl phosphonoformate.

B. Reaction Procedures for the Synthesis of the Mono-P Ester Monosodium Salts

EXAMPLES 12 TO 16

General Procedure

In a 20 mL flask, 0.5 mmol of the corresponding trimethyl ester was dissolved in 15 mL of dry acetone. NaI (75 mg, 0.5 mmol) dissolved in 2 mL acetone was added, and the mixture was refluxed for 2 h. The mixture was then cooled, filtered, and the precipitate washed with dry acetone until the wash was negative to AgNO$_3$. The final product was dried in a vacuum oven.

EXAMPLE 12

The preceding general procedure was followed wherein NaTPFA, Table I Compound (6), was synthesized. $^1$H NMR: δ (ppm) 3.68 (d, 3H, $^3J_{HP}$=1 Hz, POCH$_3$); 2.12 (d, 3 H. $^3J_{HP}$=13 Hz, SCH$_3$); $^{13}$C NMR: δ (ppm) 171.0 (d, $^1J_{CP}$=150 Hz, CO), 50.81 (POCH$_3$); 10.43 (d, $^2J_{CP}$=4 Hz, SCH$_3$); $^{31}$P NMR: δ (ppm) 18.1 (q, $^3J_{PH}$=10 Hz); Microanalysis: C%: 18.76 (Calcd), 19.27 (Found); H%: 3.15 (Calcd) 3.06 (Found); S%: 16.69 (Calcd), 17.08 (Found).

EXAMPLE 13

The preceding general procedure was followed wherein NaPTLFA, Table I Compound (8), was synthesized. $^1$H NMR: δ (ppm) 3.48 (d, 3H, $^3J_{HP}$=11 Hz, POCH$_3$), 2.22 (s, 3H, CSCH$_3$) $^{13}$C NMR: δ (ppm) 207.4 (d, $^1J_{CP}$=190, CO); 53.3 (d, $^2J_{CP}$=6 Hz, POCH $_3$); 10.1 (s, SCH$_3$); $^{31}$P NMR: δ-0.76 (q, $^3J_{PH}$=11 Hz).

EXAMPLE 14

The preceding general procedure was followed wherein NaPTNFA, Table I Compound (7), was synthesized. $^1$H NMR: δ (ppm) 4.01 (d, 3H, $^4J_{HP}$=1 Hz, COCH$_3$), 3.47 (d, 3H, $^3J_{HP}$=11 Hz, POCH$_3$); $^{13}$C: δ (ppm) 222.1 (d, $^1J_{CP}$=200 Hzs, CS); 58.9 (d, $^2J_{CP}$=8 Hz, POCH$_3$); 51.8 (d, $^3J_{CP}$=4 Hz OCH$_3$); $^{31}$P: δ (ppm) 0.26 (q, $^3J_{PH}$=11 Hz).

EXAMPLE 15

The preceding general procedure was followed wherein NaPDTFA, Table I Compound (9), was synthesized. NMR: $^1$H; δ (ppm) 3.46 (d, 3H, $^3J_{HP}$=12 Hz, POCH$_3$), 2.52 (d, 3H, $^4J_{HP}$=1 Hz, CSCH$_3$); $^{13}$C: δ (ppm) 239.0 (d, $^1J_{CP}$=150, CS); 53.3 (d, $^2J_{CP}$=6 Hz, POCH$_3$); 18.9 (s, SCH$_3$); $^3$P δ (ppm) 2.25 (q, $^3J_{PH}$=11 Hz).

EXAMPLE 16

The preceding general procedure was followed wherein NaTPTLFA, Table I Compound (11), was synthesized. NMR: $^1$H: δ (ppm) 2.20 (s, 3H, CSCH$_3$), 2.05 (d, 3H, $^3J_{HP}$=12 Hz, PSCH$_3$); $^{13}$C: δ (ppm) 204.2 (d, $^1J_{CP}$=140, CO); 12.0 (d, $^2J_{CP}$=4 Hz, PSCH$_3$); 10.5 (s, SCH$_3$); $^{31}$P δ (ppm) 22.2 (q, $^3J_{PH}$=12 Hz).

C. Prodrug Synthetic Approach

EXAMPLE 17

Isopropylidene Glycerol Scheme II Compound 1

Freshly distilled glycerol (10 g, 0. 11 mole) was shaken until dissolved with 65 mL of dry acetone containing 1 g of TsOH. After 24 hr. the solution was neutralized first with PbCO$_3$ and afterwards with Ag$_2$CO$_3$, warmed with charcoal, and shaken with a large excess of CaCl$_2$ overnight. The supernatant liquid was then filtered. The solvent was removed by rotary evaporation, and the product fractionated under diminished pressure, giving 9.5 g of the main fraction (b.p. 105–106° C./25 mm) Y=65.4%. NMR: $^1$H: δ (ppm) 4.14–4.16 (m,1H, CH), 3.65–4.0 (qxd, 2H, CH$_2$),3.57 (m, 2H, CH$_2$OH), 2.05 (sb. 1H,OH), 1.40, 1.33 (CH$_3$); $^{13}$C: δ (ppm) 109.4 (COO), 76.1 (CH), 65.7 (CH$_2$O), 62.8 (CH$_2$OH), 26.6, 25.2 (CH$_3$).

Propyl Isoproiylideneglyceryl Ether. Scheme II Compound 2

To a stirred solution of the protected glycerol (1.3 g, 10 mmol) in dry THF (20 mL) was added NaH (0.6 g, 25 mmol) portionwise at 0° C. After the reaction mixture was stirred for 30 min, 1-bromopropane (3.0 g, 25 mmol),was added. The mixture was stirred at r.t. Once the reaction was completed, 2 mL of methanol was added at 0° C. to destroy the excess of NaH. The solvent was evaporated under vacuum. (b.p. 40–42° C./50μl) The residue was extracted with ethyl acetate. The extract was washed with water. After the dried solvent was removed, 0.86 g of a yellow oil obtained (Y=49%). NMR: $^1$H: δ (ppm) 4.20–4.17 (m, 1H, CH), 3.65–4.0 (qxd, 2H, CH$_2$), 3.33–3.42 (m, 4H, CH$_2$OCH$_2$), 1.51 (m, 2H, CH$_2$CH$_2$CH$_3$), 1.27, 1.33 (s, 6H, CH$_3$CCH$_3$), 0.82 (t, 3H, CH$_3$); $^{13}$C: δ (ppm) 109.1 (COO), 74.6 (CHCH$_2$O), 73.2 (CH), 71.6 (CCH$_2$O), 66.7

(OCH2CH$_2$CH$_3$), 25.2, 26.6 (CH$_3$CCH$_3$), 22.6 (OCH$_2$CH$_2$CH$_3$), 10.3 (CH$_2$CH$_3$).

Proiyl Glyceryl Ether, Scheme II Compound 3

HCl (1 M, 2 mL) was added to a solution of 0.80 g (4.6 mmol) propyl isopropylidene ether in 3.0 mL of methanol and the reaction was stirred for 2 hr at room temperature. The reaction mixture was extracted with 3×20 mL of ethyl ether, and the combined ether extracts were dried over sodium sulfate. After removal of the solvent, the residue weighed 0.51 g (Y=83.6%). NMR: $^1$H: δ (ppm) 5.1 (m, 1H, CH), 3.37–3.68 (m, 6H, CH$_2$), 2.05 (sb, 2H, OH), 1.56 (2H, OCH$_2$CH$_2$), 0.88 (t, 3H, CH$_2$CH$_2$CH$_3$); $^{13}$C: δ (ppm) 73.3 (CH), 72.4 (CH$_2$OH), 70.5 (CH$_2$OCH$_2$), 6.42 (OCH$_2$CH$_2$), 62.7 (OCH$_2$CH$_2$), 10.4 (CH$_3$).

Benzyl Glyceryl Ether, Scheme II Compound 3, Alternative

As an alternative procedure to a stirred solution of the protected glycerol (6.7 g, 0.05 mole) in dry THF (100 mL) was added NaH (1.8 g, 0.075 mole) portionwise at 0° C. The reaction mixture was refluxed for 1.5 h, and benzyl bromide (10.3 g, 0.06 mole) was added. The mixture was stirred at room temperature. Once the reaction was completed, 2 mL of methanol was added at 0° C. to destroy the excess of NaH. The reaction mixture was extracted with 3×50 mL of ethyl ether, and the combined ether layers dried over sodium sulfate. After solvent removal, the residue of (11.9 g, Y=61%). was combined with 60 mL of 10% acetic acid, then heated (oil bath, 100° C.), until the original emulsion disappeared (about 0.5 h), After concentration, the residue was distilled in vacuo, giving 8.1 g (b.p.116–118° C./50μ) (Y=89%).

Hexadecanyl Isopropylidene Glyceryl Ether, Scheme II Compound 2, Alternative

As another alternative procedure, to prepare Scheme II, Compound 2, NaH (0.6 g, 0.025 mole) was added to 4 mL of THF containing 1.3 g (0.01 mole) of isopropylidene glycerol at 0° C. Gas was generated. After ~0.5 h, 3.0 g (0.01 mole) of hexadecanyl bromide was added dropwise. The reaction mixture was stirred for 2 h at room temperature. Methanol was added at 0° C. to destroy excess sodium hydride. The mixture was filtered, and the filtrate evaporated. The residue was extracted with 2×60 mL ethyl ether. The extract was washed with brine and water and dried over Na$_2$SO$_4$. After concentration, 2.36 g of crude product was obtained (Y=59%). NMR: $^1$H: δ (ppm) 4.24 (m, 1H, CH), 4.04–3.70 (qxd, 2H, CH$_2$), 3.44 (m, 4H, CH$_2$OCH$_2$), 1.40 (q, 2H, OCH$_2$CH$_2$, $^3$J$_{HH}$=7 Hz), 1.33 (d, 6H, CCH$_3$), 1.22 (s, 28H, CH$_2$), 0.85 (t, 3H, CH$_3$,$^3$J$_{HH}$=7 Hz).

Hexadecanyl Glyceryl Ether, Scheme II Compound 3, Alternative

Hexadecanyl isopropylidene glyceryl ether (150 mg, 0.4 mmol), 4 mg of TsOHH$_2$O and 20 mL of methanol were stirred at 0° C. overnight. Removal of the solvent gave 110 mg of a white solid, which was dissolved in 1 mL of chloroform, filtered and concentrated, and dried (vacuum oven) leaving 105 mg of product (m.p. 54–56° C.). Pure product was obtained. by recrystallization from ether, m.p. 62–64° C. NMR: $^1$H: δ (ppm) 4.93 (m, 1H, CH), 3.83–3.66 (qxd, 2H, CH$_2$OH), 3.49–3.41 (m, 4H, CH$_2$OCH$_2$), 2.80 (s,b, 2H, OH), 1.54 (m, 2H, CH$_2$CH$_2$), 1.23 (s, 26H, CH$_2$), 0.85 (t, 3H, $^3$J$_{HH}$= 7 Hz, CH$_3$); $^{13}$C: δ (ppm) 72.4 (CHOH), 71.8, 70.5 (CH$_2$OCH$_2$), 64.0 (CH$_2$OH), 31.9, 29.7, 29.6, 29.5, 29.4, 29.3,29.1, 29.0, 28.9, 22.7 (CH$_2$), 14.1 (CH$_3$); HRMS: 317.3047 (Found), 317.4056 (Calcd); Microanalysis: C%: 72.12 (Found), 72.10 (Calcd), H% 13.05 (Found), 12.74 (Calcd).

Synthesis of Scheme II Compound (5)

The Scheme II compound (4) (0.75 g, 1.3 mmole), 3 mL of pyridine, and 1 mL of acetic anhydride were stirred for 45 h at room temperature. 2 g of ice was added to the reaction mixture. 1.5 mL of chloroform was added to the mixture. The separated oil layer was then washed with 10% NaHCO$_3$ and water. The oil layer was rotary-evaporated after drying over MgSO$_4$. The residue was co-evaporated with 15 mL of toluene. 0.72 g of crude product was obtained. Purification was carried out by flash column chromatography, petroleum and ether, 7:3 as eluting agent giving 0.53 g (Y=67%) of pure compound. After standing, the product solidified, m.p. 43–44° C., NMR: $^1$H: δ (ppm) 7.40–7.18 (m, 15H, Ph-H), 5.15 (m, 1H, CH), 3.62–3.16 (m, 6H, OCH$_2$), 2.05(s, 3H, COCH$_3$), 1.48 –1.21 (m, 28H, CH$_2$), 0.84 (t, 3H, $^3$J$_{HH}$=7.0 Hz CH$_3$); $^{13}$C: δ (ppm) 170.5(C=O), 143.8, 129.0, 128.6, 127.2(Ph-C), 86.5 (cph$_3$), 71,5 (CH), 69.4, 62.5, 61.0 (OCH$_2$), 31.9, 29.7, 26.0, 22.7 (m, CH$_2$), 21.8(CH$_3$CO), 14.10 (CH$_3$), Analysis: C%: 79.96 (Found), 80.40 (Calcd), H% 9.39 (Found), 9.52 (Calcd).

Synthesis of Scheme II Compound (6)

The Scheme II compound (5) was dissolved into 2 mL of CH$_2$Cl$_2$ and 0.6 mL of 50% BF$_3$-MeOH was added at about 0° C. to room temperature, while stirred for 4 hr. After concentration, the residue was purified by preparative TLC (petroleum and ether (7+3) as eluting agent) to give 54 mg of product (R$_f$0.28) (waxy material). NMR: $^1$H: δ (ppm) 5.05 (m, 1H, CH), 3.62–3.16 (m, 4H, OCH$_2$), 2.05 (b, t, 1H, CH$_2$OH), 1.48–1.21 (m, 28H, CH$_2$), 0.86 (t, 3H, $^3$J$_{HH}$=6.9 Hz, CH$_3$), $^{13}$C: δ (ppm) 171.1 (CO), 71.75(CH), 71.3, 68.8, (OCH$_2$), 65.6(CH$_2$OH), 31.9, 29.7, 26.0 22.7(m, CH$_2$), 21.2(CH$_3$CO), 14.2 (CH$_3$).

Scheme II Compound 7 and 8

Using the hexadecanyl isopropylidene ether prepared above one conducts the steps shown in Scheme II to prepare, in succession, compounds 7 and 8 of Scheme II. Thus, 50.8 mg (0.15 mM) of scheme II compound 6 in 4 ml of THF containing 15 mg of triethylamine and about I equivalent of either ClPFA or CLTPFA was stirred at 0° C. for 2 h. After filtration and rotary evaporation of the solvent, the residue, Scheme II compound (7) was purified on silica gel (CH$_2$Cl$_2$: CH$_3$OH, 95:5): $^{31}$P NMR: δ–3.6. Scheme II Compound 7 was then hydrolyzed to Scheme II Compound 8 by methods known by those skilled in the art. The preparation of methyl chloro(methoxy)thiophosphonoformate (ClTPFA) was as follows: Lawesson's reagent (10.7 g, 97%, 0.025 mole) was dissolved in 100 ml of dry toluene at 105° C. followed by 4.0 g (0.02 mole) methyl chloro(methoxy)phosphonoformate (ClPFA) [prepared by the method of Petrov, K. A., Maklyaev, F. L. and Korshunov, M. A. J. Gen. Chem. USSR (Eng. Transl.) 29, 304–308 (1959)]. After 18 hr at reflux, the solvent was removed in vacuum and the residue extracted with hexane. The combined extracts were evaporated leaving the crude product, which was distilled in vacuo to give 0.86 g of a slightly yellow oil, b.p. 40–40.5° C. at 0.075 mm Hg. $^1$H-NMR (CDCl$_3$): δ3.97 (d, POCH$_3$, 3H, $^3$J$_{PH}$=14), 3.94 (s, COCH$_3$, 3H). $^{13}$C-NMR (CDCl$_3$): δ164.9 (d, CO,$^1$J$_{PC}$=224), 54.7 (d, POCH$_3$, $^2$J$_P$=8.5) 54.5 (d, COCH$_3$, $^3$J$_{PC}$=4.9). $^{31}$P NMR (CDCl$_3$): δ62.4. Calcd for C$_3$H$_6$O$_3$ClPS: C, 19.11; H, 3.21; S, 18.80. Found: C, 19.42, H, 3.51, S, 18.80.

EXAMPLE 18

Scheme III Compound (2)' and (4)'

To a suspension of isopropylidene glycerol (760 mg, 5.214 mmol) and NaH (240 mg, 5.88 mmole) in THF were added tetrabutyl ammonium bromide (168 mg, 0.52 mmol) at room temperature under $N_2$ followed by 4-methoxylbenzyl chloride (921 mg, 5.88 mmol). After being refluxed at 65° C. for 14 h, the reaction was quenched with methanol (1 mL) and neutrallized with $NH_4Cl$. The reaction mixture was extracted with ether and the extract was washed with brine, dried over $MgSO_4$, and concentrated in vacuo. The residue was purified with flash chromatography on silica gel with ether and hexane, 1:1. 1.54 g of yellowish oil, with a yield of about 88.6%, was obtained. NMR: $^1H$: δ (ppm) 7.27, 7.25 (dd, 4H, Ph-H), 4.51 (m, 1H, CH), 4.14 (d, 2H, $OCH_2$), 3.96 (m, 4H, $OCH_2$), 3.80 (s, 2H, $PhCH_2$), 1.42 (s, 3H, $CH_3$), 1.36 (s, 3H, $CH_3$), $^{13}C$: δ (ppm) 129.3, 130.1, 130.0, 114.1, 113.8 (Ph-C), 109.3 ($C(CH_3)_2$), 74.7 (CH), 73.1, 70.7, 66.9 ($OCH_2$) 55.1($OCH_3$), 26.75, 25.3 ($CH_3$). HRMS: 252.1371(Found), 252.1361 (Calcd), Analysis: C%: 66.85(Found) 66.65(Calcd), H%: 7.58 (Found), 7.99 (Calcld). 3-p-methoxybenzyl-1,2-isopropylidene glyceryl ether, Scheme III compound (2)' was deprotected in 10 mL 10% acetic acid at 65° C. for 1 hr. The reaction mixture was lyophilized and the residue was purified by flash column chromatography, ethyl acetate as eluting agent. NMR: $^1H$, $^3C$ consistent with structure.

Scheme III compounds (3)', (5)' and (6)'

The R group was hexadecanyl. Scheme III compound (4)' (1.15 g 4.7 mmol), powdered KOH (1.06 g, 19 mmol), hexadecyl bromide (5.73 g, 20 mmole) and 25 mL toluene were mixed. The reaction mixture was refluxed for 16 hr at room temp. Next, 20 mL of water was added and the oil layer separated. The aqueous layer was washed by toluene and the combined oil phases washed with water brine. After drying over $Na_2SO_4$ and concentrating, 7.1 g of crude product, Scheme III Compound (3)', was obtained. This was purified by flash chromatography (using hexane and ethyl ether, 9:1). $R_f$=0.44. NMR: $^1H$, $^{13}C$ consistent with structure.

To a mixture of Scheme III Compound (3)' (1.0 g, 1.5 mmol) in $CH_2Cl_2$ (9 nL) and $H_2O$ (0.5 mL) was added DDQ (2,3-dichloro-5,6-dicyanobenzoquinone, 0.36 g, 1.58 mmol). The reaction mixture turned progressively redbrown. After 15 min at room temperature the reaction mixture was filtered, and the filtrate was evaporated in vacuo giving a yellowish solid (0.75 g). This was purified by flash column chromatography (using hexane and ether, 3:1) to give Scheme III Compound (5)', m.p. 50–51° C. (Y=93.8%) NMR: $^1H$: δ (ppm) 3.68 (m,1H, CH), 3.60–3.39 (m, 8H, $OCH_2$), 2.16–2.13 (dd, 1H, $CH_2OH$), 1.31–1.24 (m, 56H, $CH_2$), 0.86 (t, 6H, $^3J_{HH}$=6.9 Hz); $^{13}$ C: δ (ppm), HRMS: 540.5568 (Found), 540.5481 (Calcd), Analysis: C%:. 77.39 (Found), 77.71 (Calcd), H%: 13.23 (Found), 13.42 (Calcd). Scheme III Compound (6)' (90 mg, 0.28 mM) and 2 ml pyrimidine were dissolved in 1.5 ml chloroform together with 1 equivalent of CIPFA or CLTPFA, which was added at –10° C. The temperature was allowed to rise to r.t., then the reaction mixture was filtered and the filtrate concentrated by rotary evaporation. The residue was purified by column chromatography on silica gel ($CH_2Cl_2$:$CH_3OH$, 95:5) giving Scheme III Compound (6)' with $R_f$=0.26. $^{31}P$ NMR: δ–3.6. Scheme III Compound (7)' was demethylated by methods known to those skilled in the arts.

The following references, discussed above, are all incorporated herein by reference: U.S. Pat. No. 5,183,812 to McKenna; D. W. Hutchinson, et al., "Synthesis and Biochemical Properties of Some Pyrophosphate Analogues", Biophosphates and Their Analogues-Synthesis, Structure, Metabolism and Activity, K. S. Bruuzik and W. J. Stec (Eds.), Elsevier Science Publishers, B. V., 1987,.441,–450; Helgstrands, et al., Science, 201:819–821 (1978)); J. Levillain, et. al., J. Am. Chem. Soc. 115:8444–8446, 1993; L. V. Kovalenko, et al., Russian J. General Chemistry 64, Part 1, 1456–1459, 1994); D. W. Grisley, Jr., J. Org. Chem. 26, 2544–2546, 1961; U.S. Pat. No. 5,072,032 to C. E. McKenna, et al.; Irwin B. Douglass, J. Am. Chem. Soc. 78:6070 (1956); S. Masson et al., Tetrahedron Lett. 31 1151 (1990); Ryu, et al, J. Med. Chem. 25, 1322–1329 (1982); M. Fuji, et al., J. Org. Chem., 62, 6804 (1997); K. Hostetler, et al., Antiviral Research, 31, 59–67 (1996); and Dieter Martin and Wolfgang Mocke, Chemishe Berichte, 98 (7), 2059 (1965).

The compounds of this invention are proposed for use in standard assays for HIV-I reverse transcriptase. The procedures therefor that can be used, mutatis mutandis, and described in McKenna U.S. Pat. No. 5,072,032, the disclosure of which is incorporated herein by reference. They also are proposed for use for the treatment of herpes virus infections in AIDS patients, in medical uses such as antiviral compounds, and in agricultural uses such as pesticides.

Although the foregoing invention has been described in some detail by way of illustration and example for purposes of clarity and understanding, it will be obvious that various modifications and changes which are within the knowledge of those skilled in the art are considered to fall within the scope of the appended claims.

What is claimed is:

1. A substantially pure thio-analog of phosphonoformic acid comprising the formula:

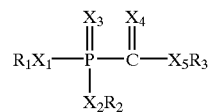

wherein $R_1$ and $R_2$ are each independently selected from alkyl, aryl, H, and cation, $R_3$ is independently selected from alkyl, aryl, H, cation, and a prodrug moiety, and $X_1$, $X_2$, $X_3$, $X_4$, and $X_5$ are each independently selected from O and S, provided that:

(a) at least one of $X_1$–$X_3$ is S;

(b) when $X_1$ is S, then either (i) $R_1$ or $R_2$ is alkyl, aryl, or H, or (ii) at least one of $X_2$, $X_3$, $X_4$, and $X_5$ is also S;

(c) $R_1$ and $R_2$ are different provided that $R_3$ has 1 carbon atom.

2. A substantially pure thio-analog of phosphonoformic acid comprising the formula:

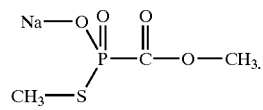

3. A substantially pure thio-analog of phosphonoformic acid comprising the formula:

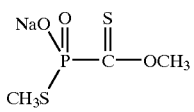

4. A substantially pure thio-analog of phosphonoformic acid comprising the formula:

5. A substantially pure thio-analog of phosphonoformic acid comprising the formula:
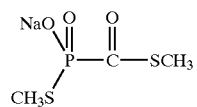
* * * * *